United States Patent [19]

Di Giovanni et al.

[11] Patent Number: 4,487,205

[45] Date of Patent: Dec. 11, 1984

[54] NON-METALLIC, BIO-COMPATIBLE HEMOSTATIC CLIPS

[75] Inventors: John Di Giovanni, Irvington; Glen C. Dorband, Somerville; Donald M. Golden, Cherry Hill, all of N.J.

[73] Assignee: Ethicon, Inc., Somerville, N.J.

[21] Appl. No.: 371,845

[22] Filed: Apr. 26, 1982

[51] Int. Cl.³ ............................................. A61B 17/12
[52] U.S. Cl. .................................. 128/326; 128/346; 251/10
[58] Field of Search ............... 128/325, 326, 346, 337; 251/9, 10

[56] References Cited

U.S. PATENT DOCUMENTS

| 1,708,432 | 4/1929 | Sprigg | 128/346 |
| 2,498,372 | 2/1950 | Kortlucke et al. | 128/346 |
| 3,040,749 | 6/1962 | Payton | 128/346 |
| 4,112,951 | 9/1978 | Hulka et al. | 128/346 |

FOREIGN PATENT DOCUMENTS 2525650 12/1976 Fed. Rep. of Germany ...... 128/346

Primary Examiner—Dalton L. Truluck
Attorney, Agent, or Firm—Robert L. Minier

[57] ABSTRACT

Hemostatic clips made from non-resilient polymeric materials. The clips comprise a pair of leg members rotatable about a hinge portion to be closed over a vessel.

6 Claims, 8 Drawing Figures

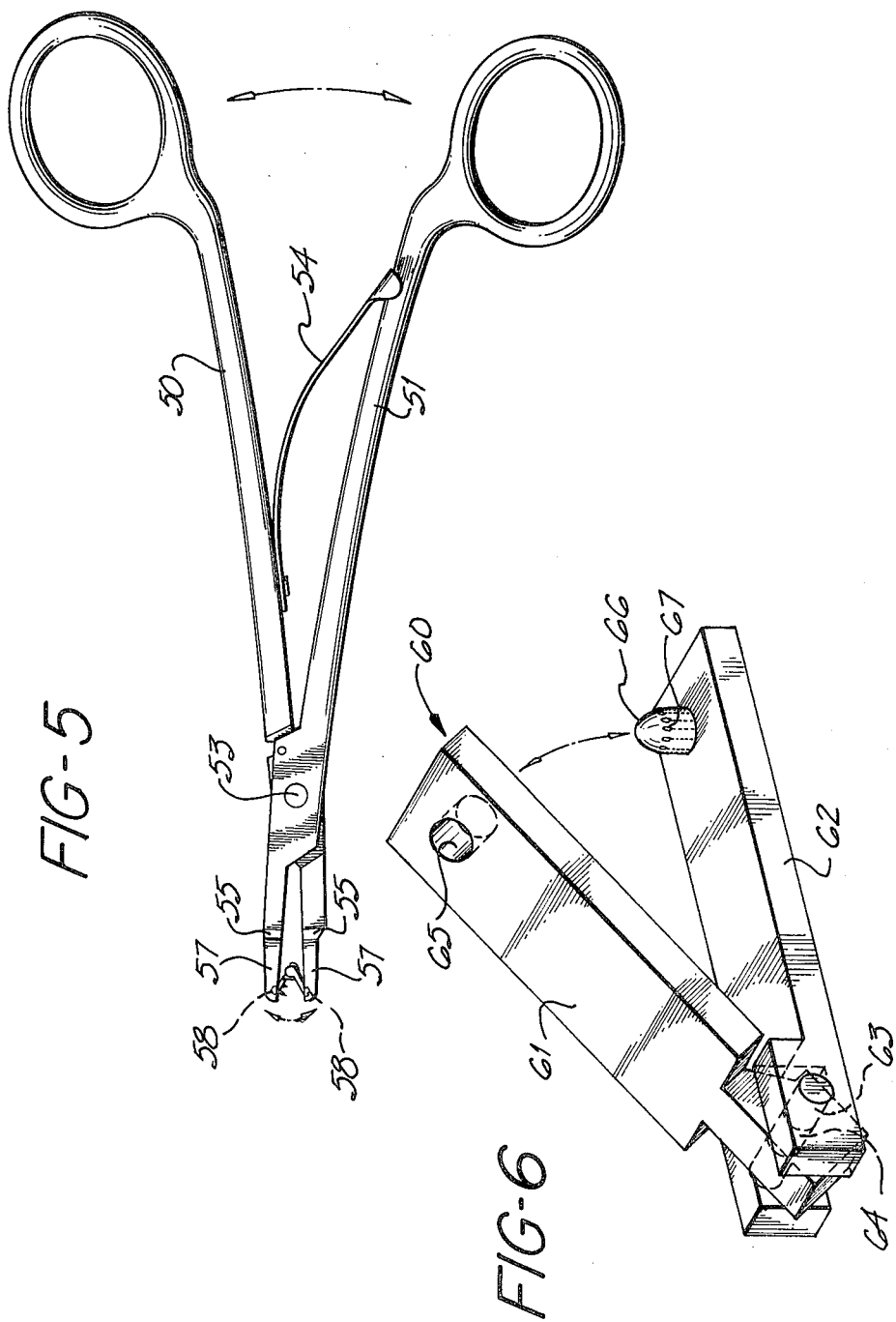

NON-METALLIC, BIO-COMPATIBLE HEMOSTATIC CLIPS

The present invention relates to hemostatic clips, and more particularly to hemostatic clips fabricated from biocompatible polymeric materials which may be absorbable or non-absorbable in body tissue.

BACKGROUND OF THE INVENTION

In many surgical procedures, it is often necessary to ligate a plurality of vessels within the surgical site. The vessels may be severed downstream of the ligated portion. In some instances, the vessels may be ligated in spaced apart areas and the portion of the vessel between the ligations removed. The purpose of ligating vessels is to maintain the surgical site free from an excess of blood and reduce blood loss in the patient. Also in certain surgical procedures where tumors and the like are to be removed, the tumor or organ may have to separated from certain vessels. Before separating, the vessels are ligated. Once a blood vessel is completely shut off, hemostatsis, that is, the natural closing of the end of the vessel so as to stop blood flow, will occur in several days depending on the vessel. The body, in the meantime, will continue to allow blood flow around the ligated area through appropriate capillaries and secondary vessels with the natural physiological function of the body enlarging these bypass vessels until adequate blood flow is obtained. Hence, when ligating the vessel, there should be positive stoppage of the blood flow in the main vessel. Failure to provide complete stoppage may cause blood loss in the patient and may also disrupt the natural hemostasis and concurrent manufacture of new paths of blood flow in the patient.

In the past, this closing of the vessel was usually accomplished using ligatures; i.e., filaments or threads which the doctor tied around the vessel to be closed. This is a time consuming process and one wherein positive closure of the vessel is not always accomplished. In recent years, hemostatic clips have replaced ligatures in surgical procedures to close blood vessels and other fluid ducts. Very often these hemostatic clips are narrow U or V shaped strips formed of tantalum or stainless steel which are capable of being deformed and possess sufficient strength to retain the deformation when clamped about a blood vessel. The closing force is developed by the deformation of the metal. We know of no polymeric materials that can be used in this type of clip. The polymeric materials are either too resilient and will not maintain the closed position or too brittle and break when deformed to the extent required to surround and close a vessel.

In co-pending commonly assigned patent application Ser. Nos. 276,131 filed June 22, 1981 and 282,165 filed July 31, 1981, there are disclosed hemostatic clips made from bio-compatible polymeric materials which are absorbable or nonabsorbable in body tissue. These clips comprise a pair of leg members connected at their proximal ends by a resilient hinge section and terminating at their distal ends in a locking latch means. The distal end of one of the leg members comprises a deflectable hook section. The distal end of the other leg member is configured to be engaged by the hook section and the leg members are pivoted about the hinge to close the clip about a blood vessel. These clips have been found very satisfactory for ligating blood vessels. However, there are certain polymeric materials that do not have the required resiliency to be used in such clips. For example, it is very difficult to make lactide and glycolide polymers and copolymers which have sufficient resiliency to produce a resilient hinge on a clip that will function to maintain a blood vessel closed. Also, these polymers are relatively brittle so that they cannot be deformed about a blood vessel similar to the way a metal clip is used to close a blood vessel.

What we have discovered is an improved ligating clip structure which allows the clip to be made from substantially non-resilient and non-deformable materials, yet produces a clip which adequately closes a blood vessel for a sufficient period of time to provide hemostatsis and makes a suitable hemostatic clip.

Our new clip is configured to be readily and easily manipulatable so that the clip may be opened and closed about a blood vessel with a minimum of manipulative actions. Furthermore, our new clip may be manufactured using simple molding techniques well known in the art and is inexpensive to purchase.

SUMMARY OF THE PRESENT INVENTION

A hemostatic clip of a relatively non-resilient and nondeformable polymeric material. The clip comprises a pair of leg members with the leg members being attached or detachable at their proximal ends. The leg members diverge from each other when the clip is in the open position and the leg members are substantially parallel when the clip is in the closed position. The leg members meet at their proximal ends in a freely rotatable hinge portion. The hinge portion comprises a slot disposed at the proximal end of one leg member with a pin spanning the slot to provide openings on both sides of said pin. The other leg member terminates at its proximal end in a complimentary hook or eye. The hook or eye is narrower than the body of the leg member and is adapted to fit around at least a portion of the pin of the other leg member and is rotatable about the pin. This allows the leg members to be moved from their diverging open position to a closed position. Our new clip includes locking means for maintaining the legs substantially parallel when the clip is in the closed position. In certain embodiments of the clip of the present invention, there is a latch means connected to a portion of one of the leg members to maintain the legs open or diverging until sufficient force is placed on the two legs to close them. In other embodiments of the present invention, the locking means includes a pin vertically disposed from the distal end of one of the leg members which fits into an appropriate opening or hole disposed at the distal end of the opposite leg member. The pin and hole may be sufficiently tight to hold the two legs together (frictional fit) or they may have various mechanical means disposed on their surfaces to insure the two legs and lock them together (interference fit). In certain embodiments of the present invention, a raised area may be disposed from the central portion of one of the leg members which cooperates with a recess in the opposite leg member to prevent lateral movement between the legs when the clip is closed.

BRIEF DESCRIPTION OF THE DRAWINGS

The present invention will be more fully described in conjunction with the accompanying drawings wherein:

FIG. 5 is a side view showing an instrument for applying the clips of the present invention;

FIG. 6 is a perspective view of an embodiment of a hemostatic clip of the present invention;

DETAILED DESCRIPTION OF THE INVENTION

Figure 1:
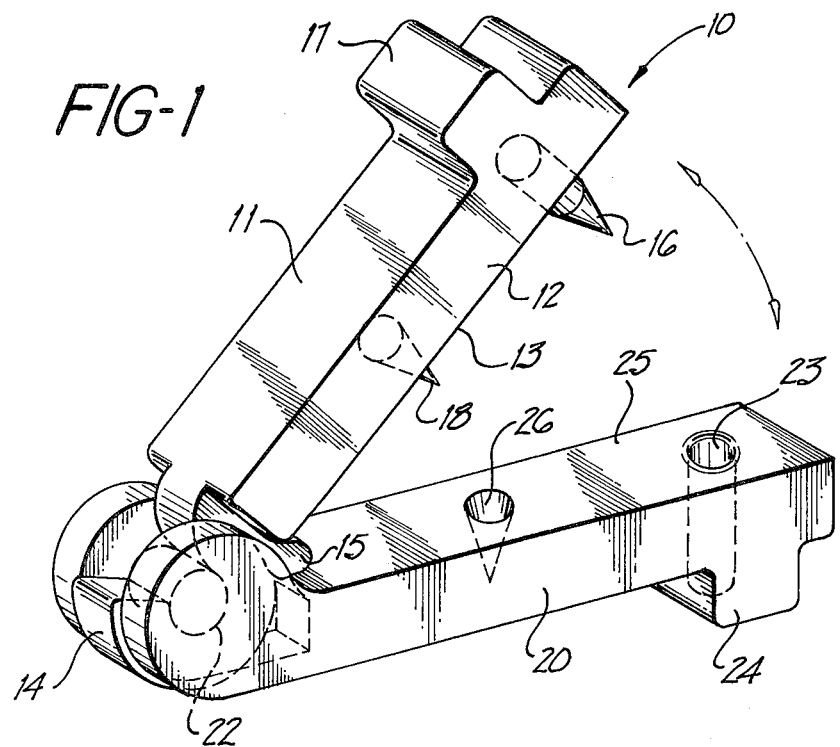
FIG. 1 is a perspective view of a new clip of the present invention in the open position.

Referring to the drawings in FIG. 1, there is shown a clip 10 of the present invention in the open position. The clip comprises a first leg member 11 having a body portion 12 with the vessel clamping surface 13. The leg member terminates at its proximal end in a hook portion 14. Also at the proximal end of this leg member there is a protrusion 15 serving as a latch means to prevent closing of the clip until sufficient pressure is applied to spring the latch. Disposed from the vessel clamping surface at the distal end of the leg member is a pin 16. Disposed on the opposite surface of the leg member is a suitable knob 17 for use in applying the clip. Also disposed from the vessel clamping surface in the center portion of the body portion is a barb 18. The opposite or second leg member 20 terminates at its proximal end in a slot and pin 22 for accepting the hook of the first leg member. The second leg member terminates at its distal end in a suitable opening 23 for accepting the pin of the first leg member. On the outer surface of this leg member there is also a knob 24 that is used in applying the clip to a blood vessel. Disposed from the vessel clamping surface 25 in the center portion there is a suitably configured recess 26 for accepting the barb of the first member.

Figure 2:
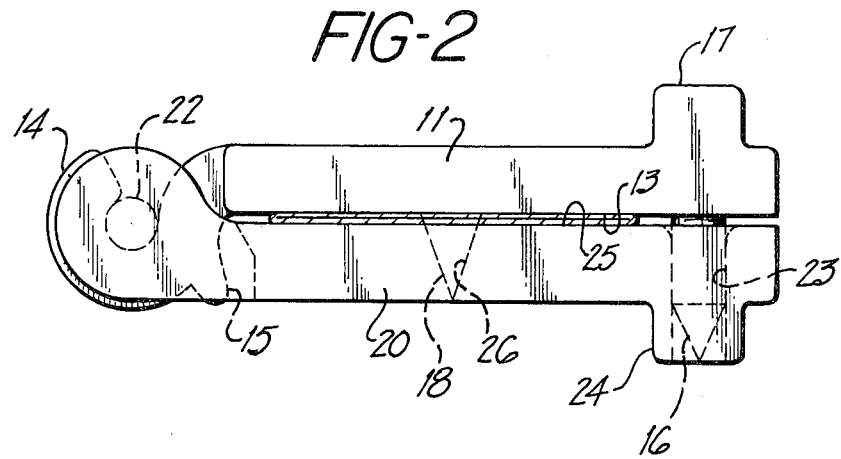
FIG. 2 is a side view of the clip of FIG. 1 in the closed position.

In FIG. 2, the clip is shown in its closed position with the vessel clamping surfaces 13 and 25 parallel and with the pin from the first leg member inserted in the opening of the second leg member.

Figure 3:
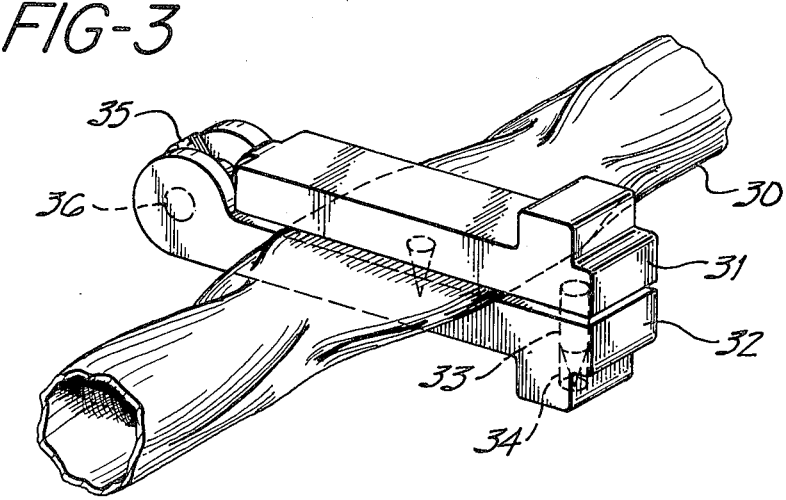
FIG. 3 is a schematic perspective view showing the clip of the present invention closed about a blood vessel.

FIG. 3 shows the clip described in conjunction with FIGS. 1 and 2 closed about a blood vessel 30 by urging the distal ends of the two leg members 31 and 32 together until the pin 33 is inserted in the opening 34 and is locked therein. The hook 35 of the first leg member rotates about the pin 36 of the second leg member to allow the vessel clamping surfaces to be brought relatively parallel to one another and to be closed about the blood vessel.

Figure 4:
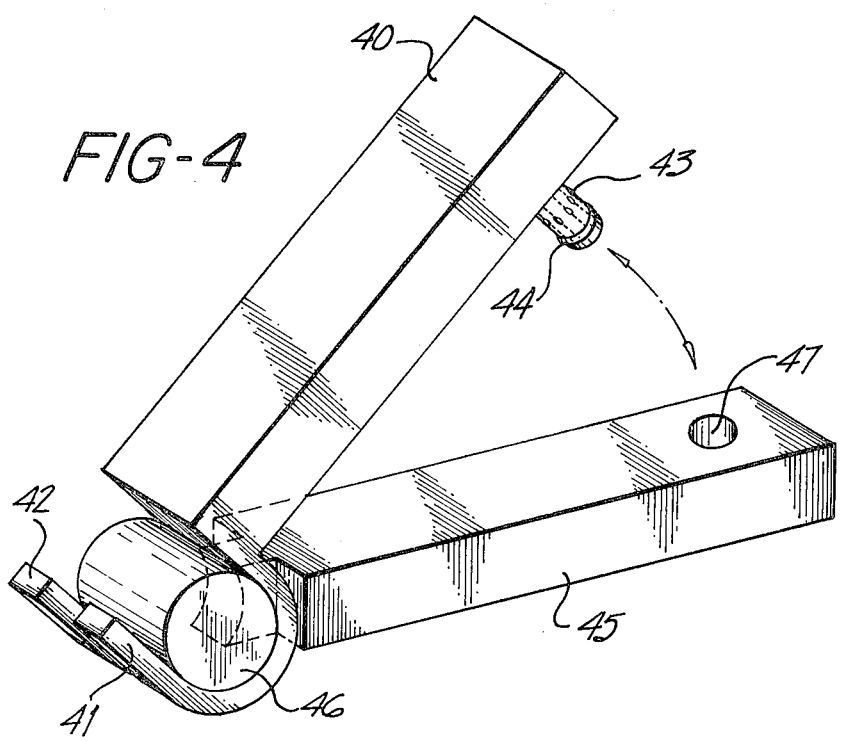
FIG. 4 is a perspective view of another embodiment of a hemostatic clip in accordance with the present invention.

In FIG. 4 there is shown another embodiment of the clip of the present invention. In this embodiment, the first leg member 40 terminates at its proximal end in a pair of hook members 41 and 42 one of each of which extend from the outer lateral sides of said leg member. The distal end of this leg member terminates in a protrusion 43 having an extended or raised area 44 about the circumference at its lower end thereof. The second leg member 45 terminates at its proximal end in a pin 46 which extends the width of the leg member. The leg member 45 is narrowed or indented adjacent the pin. The hooks of the first leg member are placed about the periphery of the pin and are rotatable thereabouts. On rotating the hook members about the pin, the vessel clamping surfaces of the two leg members are brought together and are substantially parallel. The protrusion 43 extending from the vessel clamping surface of the first leg member 40 at its distal end is inserted into the opening 47 in the distal end of the second leg member 45. This protrusion is inserted sufficiently so that the extension 44 at the outer periphery of the protrusion passes through and beneath the second leg member to lock the two leg members together.

FIG. 5 illustrates a forceps type ligating clip applier comprising two handle members 50 and 51 crossing at a hinge point 53 and maintained in a normally open position by a spring 54. One handle extends beyond the hinge forming a jaw member 55 while the extension of the other handle also forms a corresponding jaw member 56.

The jaws are identically designed and are provided with channels 57 extending rearwardly from the tips of the jaws to guide the clip. Each channel is provided with a recess 58 disposed transverse of the channel and near the distal end thereof. These recesses are sized to accept the knobs at the distal ends of the clips. The recesses are in alignment when the jaws of the applier are closed. Usually the channels forward of the recesses are slightly deeper than to the rear to prevent any interference in closing of the clip. The clip is initially loaded in the applier in its open position. The jaws of the applier are then moved or positioned over the vessel to be ligated and the jaws of the applier closed and the clip locked on to the vessel. The applier is then removed and the clip allowed to remain with the blood vessel.

Referring to FIG. 6, there is shown another embodiment of a clip of the present invention. The clip 60 comprises a first leg member 61 and a second leg member 62. The leg members are connected at their proximal ends by a pin 63 on the second leg member 62 and an eye 64 on the first leg member 61. The leg members are intermolded in this configuration with the eye rotatable about a portion of the periphery of the pin. The distal end of the first leg member has an opening 65 disposed therein. The distal end of the second leg member includes a protrusion 66. The protrusion includes raised areas 67 disposed about the periphery to provide an interference fit with the opening when the clip is closed.

Figure 7:
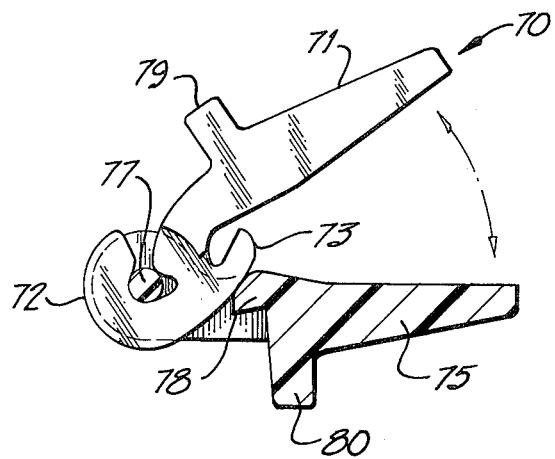
FIG. 7 is a side view of another embodiment of a hemostatic clip of the present invention with the clips in the open position.
Figure 8:
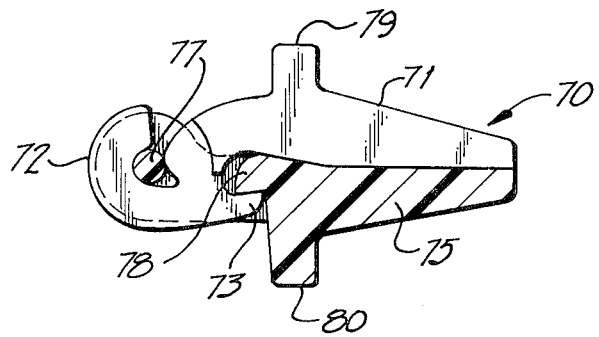
FIG. 8 is a side view of the clip shown in FIG. 7 with the clip in the closed position.

FIGS. 7 and 8 show yet another embodiment of the novel clips of the present invention. In this embodiment, the locking means for the clip is disposed adjacent the hinge at the proximal end of the leg members rather than at the distal end of the leg members as in the other embodiments. The clip 70 comprises a first leg member 71 having a body portion with a vessel clamping surface. The leg member terminates at its proximal end in a hook portion 72. Also at the proximal end of this leg member there is a reverse hook means 73. The opposite or second leg member 75 terminates at its proximal end in a slot and a pin 77 for accepting the hook of the first leg member. A portion of the body of the second leg member adjacent the proximal end is cut away to form an engaging means 78. When the clip is in the open position as seen in FIG. 7, the reverse hook means 73 engages the upper surface of the second leg member to maintain the clip in the open position. When pressure is applied to the distal end of the leg members to close the clip the reverse hook is depressed about the end of the second leg member and the engaging means caught by the reverse hook to lock the clip in the closed position as shown in FIG. 8. The opposite outer surfaces of the leg members include raised cylindrical bosses 79 and 80 that are used to manipulate the clip in a suitable applying instrument for applying hemostatic clips to blood vessels.

The clips of the present invention may be constructed in various sizes according to their intended function. Hemostatic clips are usually less than 6 millimeters in length and 1½ millimeters in width and have a vessel clamping surface of about 3 millimeters in length. The dimension of the clip may be reduced by about 50 percent for certain applications in microsurgery. Larger clips for special hemostatic applications and other functions such as closure of overducts may have about double those of a typical hemostatic clip. The various sizes of the clips may be preferably matched with individual appliers having jaws tailored to the size of the clip for best performance.

The clips of the present invention are most conveniently molded of biologically acceptable polymeric materials which may be absorbable or non-absorbable by body tissue. Preferred absorbable polymers and copolymers include those of glycolide, latide, poly(p)-dioxanone. Preferred nonabsorbable polymers include nylon, polyester, polypropylene. All these materials have been demonstrated to be biologically acceptable when used as sutures or other implantable medical devices.

The clips of the present invention may be easily and economically manufactured by injection molding or other suitable molding techniques well known in the art.

Having now described the present invention and certain specific embodiments therein, it will be readily apparent to those skilled in the art that many variations and modifications may be made to the present invention without departing from the spirit and scope thereof.

What is claimed is:

1. A hemostatic clip of a relatively nonresilient and nondeformable polymeric material comprising a pair of leg members, said leg members having opposed vessel clamping surfaces, said leg members being attached or attachable at their proximal ends in a rotatable hinge portion, said hinge portion comprising a pin integral with and disposed at the proximal end of one of the leg member and a complementary hook or eye integral with and disposed at the proximal end of the other leg member, a protrusion adjacent said hook or eye member causing the leg members to diverge from one another to hold the clip in an open position, said pin being sized to fit within the hook or eye, said hook or eye contacting the periphery of the pin and being rotatable about a portion of the periphery of the pin to move said protrusion out of its original position to allow said leg member to be moved from an open position wherein the legs diverge from one another to a closed position wherein the legs are substantially parallel with the vessel clamping surfaces adjacent one another and locking means for maintaining the legs substantially parallel when the clip is in a closed position.

2. A hemostatic clip according to claim 1 wherein the locking means comprises a protrusion extending from the vessel clamping surface of one leg member and a corresponding opening in the vessel clamping surface of the other leg member whereby when the clip is closed the protrusion fits into the opening to lock the leg members together.

3. A hemostatic clip according to claim 2 wherein the protrusion includes raised areas on its surface to provide an interference fit with said opening.

4. A hemostatic clip according to claim 1 wherein the locking means comprises a reverse hook means disposed adjacent the proximal end of one leg member and adapted to engage a portion of the other leg member when the clip is in the closed position.

5. A hemostatic clip according to claim 1, 2 or 4 wherein the outer surfaces of the leg members include clip applying means extending transverse of the outer surface and being positioned to be engaged by the jaws of a suitable forceps type clip applier.

6. A hemostatic clip according to claim 1, 2 or 4 wherein the pin at the proximal end of the first leg member is disposed in a slot extending from said leg member providing an opening between the pin and the body of the leg member and the hook on the proximal end of the second leg member being sized to fit within the opening about said pin.

* * * * *